United States Patent [19]

Louwes

[11] Patent Number: 5,164,192
[45] Date of Patent: Nov. 17, 1992

[54] EFFERVESCENT COMPOSITION FOR ORAL REHYDRATION

[75] Inventor: Herman D. Louwes, Weesp, Netherlands

[73] Assignee: Duphar International Research B.V., Weesp, Netherlands

[21] Appl. No.: 646,478

[22] Filed: Jan. 24, 1991

Related U.S. Application Data

[63] Continuation of Ser. No. 474,334, Feb. 2, 1990, abandoned.

[30] Foreign Application Priority Data

Feb. 7, 1989 [NL] Netherlands .................. 8900294
May 9, 1989 [NL] Netherlands .................. 8901160

[51] Int. Cl.$^5$ .................. A61K 9/46; A61K 9/14; A61K 33/10; A61K 31/715
[52] U.S. Cl. .................. 424/466; 424/715; 424/717; 424/488; 424/499; 514/867
[58] Field of Search .................. 424/466, 717; 514/867

[56] References Cited

U.S. PATENT DOCUMENTS

| | | | |
|---|---|---|---|
| 3,873,694 | 3/1975 | Kanig | 424/717 |
| 4,036,228 | 7/1977 | Theeuwes | 424/466 |
| 4,164,568 | 8/1979 | Bywater | 514/867 |
| 4,650,669 | 3/1987 | Alexander et al. | 424/466 |
| 4,704,269 | 11/1987 | Korab | 424/466 |
| 5,037,657 | 8/1991 | Jones et al. | 424/466 |
| 5,038,396 | 8/1991 | Gjerlov | 424/195.1 |

OTHER PUBLICATIONS

Scan. J. Infect. Dis. 18, (1986), pp. 65–70.

*Primary Examiner*—Thurman K. Page
*Assistant Examiner*—E. J. Webman
*Attorney, Agent, or Firm*—Stevens, Davis, Miller & Mosher

[57] ABSTRACT

The invention relates to an effervescent product for the preparation of an oral rehydration solution for the treatment of diarrhoea. The product comprises oligosaccharides and/or disaccharides, and/or monosaccarides and/or amino acids as energy carriers, and (bi)carbonate and a bicarbonate precursor as alkalizing substances. The product has the form of a tablet or a powder.

5 Claims, No Drawings

EFFERVESCENT COMPOSITION FOR ORAL REHYDRATION

This application is a continuation of application Ser. No. 474,334, filed Feb. 2, 1990, now abandoned.

The invention relates to an effervescent product for the preparation of an oral rehydration solution (OR-solution) for the treatment of diarrhoea.

Diarrhoea is not only a disease occurring frequently in man (for example children in developing countries), but diarrhoea also causes enormous economic losses in (intensive) cattle breeding, notably in young calves and piglets. Diarrhoea also is a frequently occurring phenomenon in companion animals.

Diarrhoea is associated with the loss of water (dehydration), the loss of electrolytes (mainly $Na^+$, $Cl^-$ and to a lesser extent $K^+$, $HCO_3^-$) and with a metabolic acidosis (acidification as a result of excessive lactic acid production).

The vast majority of the patients who do not survive the diarrhoea die from dehydration, metabolic acidosis and/or disturbances of the electrolyte balance. Mortality can be prevented by treating these symptoms effectively. It has been found that the patient often is able to eliminate the cause of the diarrhoea afterwards.

The cause of diarrhoea may be both infectious and non-infectious. Because the aetiology often is unknown and a causal treatment of the diarrhoea often is not possible, a symptomatic treatment is indicated. Liquid therapy, preferably orally, is the first-choice therapy because it is effective in all of bacterial, viral and non-infectious forms of diarrhoea. In this case it is not necessary to make a precise diagnosis.

The oral liquid therapy consists of the administration of an oral rehydration solution (OR-solution). This OR solution comprises water, electrolytes, absorption-promoting substances and alkalizing substances, as a result of which dehydration, loss of electrolytes and acidosis are controlled effectively.

Because domestic animals suffering from diarrhoea very often are hypoglycaemic, the total energy content of the oral rehydration solution is of importance. The energy must preferable be present in the form of carbohydrates. The OR solution must be iso-osmotic; hypertonic solutions in fact cause an osmotic diarrhoea and delay the emptying of the stomach and hence the availability of the OR solution.

A citrate-containing effervescent tablet for the preparation of an oral rehydration solution for human application is known from Scan. J. Infect. Dis. 18 (1986), pp. 65-70. The solution prepared by means of this effervescent tablet proved to be as active for the treatment of diarrhoea in adults and children as the known bicarbonate-containing oral rehydration (OR) solution recommended by the World Health Organization (WHO).

The above-mentioned effervescent tablet has the following composition:

| | |
|---|---|
| glucose (0 aq) | 2182 mg |
| sodium chloride | 421 mg |
| potassium chloride | 180 mg |
| citric acid | 691 mg |
| sodium bicarbonate | 302 mg |
| saccharin sodium | 50 mg |

Dissolved in 120 ml of water the solution has the following composition:

| | |
|---|---|
| $Na^-$ | 90 mmol/l |
| $K^-$ | 20 mmol/l |
| $Cl^-$ | 80 mmol/l |
| citrate ($H_2$ citrate$^-$) | 30 mmol/l |
| glucose | 100 mmol/l |

This composition is substantially identical to the OR solution of the WHO, with the proviso that 30 mmol of citrate ($H_2$ citrate) have been used instead of bicarbonate.

The invention relates to an OR formulation which can be tabletted without any auxiliary substances (optionally lubricants may be added) by means of direct compression. The formed effervescent tablet dissolves completely without stirring in lukewarm water within a few minutes. Existing OR products are commercially available in the form of powders packed in sachets, unsplit powders or unsplit liquid concentrates. The preparation of the OR-solution in this manner using these compositions is less simple than with the effervescent composition according to the invention.

In addition, the formed OR solution has been specifically prepared for use either in domestic animals or companion animals, this in contrast with most of the available OR products.

The resulting iso-osmotic OR solution comprises:
a. an electrolyte composition with which losses are compensated and with which a rapid rehydration is ensured.
b. lactose and/or maltodextrins as a result of which the required energy occupies a smaller ($\frac{1}{2}$ to 1/5) part of the osmotic space than when glucose alone is used.
c. a combination of directly and indirectly acting alkalizing substances, as a result of which the metabolic acidosis is cured safely and effectively.

Usually the following auxiliary substances have to be used for the production of the effervescent tablets:
bicarbonate (or carbonate salts)
citric acid (or other solid organic acids, for example, gluconic acid, fumaric acid, maleic acid, tartaric acid, adipic acid).

Bicarbonate reacts with citric acid in the presence of water, citrate, $H_2O$ and $CO_2$ being formed. As a result of the $CO_2$ development the effervescent effect occurs, as a result of which the tablet dissolves within a few minutes. With a strong effervescent effect a homogeneous solution is obtained without stirring.

Bicarbonate and citric acid are present in the oral rehydration effervescent tablet according to the invention not only as an "auxiliary substance", but also as a therapeutically active substance. As a matter of fact, the excess of bicarbonate and the formed citrate together form the mixture of directly and indirectly acting alkalizing substances which are reponsible for the effective and safe neutralization of the metabolic acidosis.

The OR solution which is obtained after dissolving the effervescent product has an ideal electrolyte composition, as a result of which the loss of electrolytes caused by the diarrhoea is fully compensated and the absorption of water from the intestine is optimally stimulated. Sodium ions play an important part in the absorption of water. By means of the absorption of sodium via active carriers an osmotic gradient is formed across the intestinal epithelium as a result of which water also diffuses passively. Therefore, the total quantity of sodium present in the OR product is of importance. The sodium concentration in the composition for the domestic animals is approximately 120 mmol/l, which is considerably higher than in the known OR products. Rehydration, therefore, will take place rapidly. Because a hypernatremia easily occurs in companion animals, the sodium concentration in this composition is 50–90 mmol/l.

During diarrhoea the potassium content in the plasma is increased. In fact, as a result of the metabolic acidosis an exchange of intracellular potassium and extracellular hydrogen ions occurs. In spite of this increased content of potassium in the plasma, OR solution must comprise potassium so as to replace potassium lost via the faeces. Because during diarrhoea net calcium is still absorbed and the body has the disposal of large reserve stocks, addition of calcium is not necessary. Magnesium may be added to OR solutions because small quantities of magnesium are lost.

The OR solution formed by means of the invention comprises a combination of so-called absorption-promoting substances. These are substances which promote the active absorption of sodium and hence also the absorption of water.

Glucose, but also galactose, promote the active sodium transport.

The up-take of sodium is also promoted by amino acids (L-configuration). There are probably several types of amino acid/sodium carriers in the intestine. In order to enable a maximum sodium up-take, the OR solution must comprise glycine or other amino acids. The sodium up-take in the intestine is also promoted by, for example, bicarbonate, citrate and volatile fatty acids.

Absorption-promoting substances present in the solution prepared by means of the OR effervescent tablet are:
glucose and galactose (splitting products of lactose) or
   glucose and glucose dimers (splitting products of maltodextrin)
glycine.
citrate and bicarbonate.

Because sodium and absorption promoting substances, for example, glucose, galactose and glycine, are preferably absorbed together by the active carrier systems in the intestinal epithelium, the molar ratio of substrate and sodium in the OR liquid has to be at least 1:1. Any excess of substrate will stimulate the absorption of endogenic sodium and water.

The total energy content of OR solutions is important because domestic animals suffering from diarrhoea often are hypoglycaemic. The energy must be present substantially in the form of carbohydrates (for example, glucose). A 5% glucose solution which covers only a part of the energy need of the patient, however, is already iso-osmotic. Higher glucose concentrations give hypertonic solutions. Hypertonic solutions inhibit the stomach-emptying rate and hence the availability of the OR solution. Moreover they give rise to an osmotic diarrhoea. According to the invention this problem has been solved by replacing glucose with oligosaccharides and/or disaccharides. Oligosaccharides, for example, maltodextrins and disaccharides, for example, lactose, have a higher energy content ($\pm 5$ to 2 times) than glucose, while the osmotic value per mol is equal. Maltodextrins are rapidly split in the intestines of monogastric animals to glucose and glucose dimers.

Young ruminants, on the contrary are not capable of decomposing maltodextrins or other oligosaccharides because they do not dispose of the splitting enzymes d-amylase and maltase. Because (young) ruminants cannot dispose of the enzyme lactase, lactose has been chosen as the energy source in the composition for these animals. 1 Molecule of lactose is split by the enzyme lactase into 1 molecule of glucose and 1 molecule of galactose. By processing lactose and/or maltodextrins, more energy can be processed in an isotonic solution, so that a hypoglycaemia associated with diarrhoea can be controlled more effectively. Moreover, more "osmotic space" can be reserved in the OR solution for other components. For example, space has been reserved for extra glycine in the OR solution for companion animals. Recent human research has demonstrated that glycine (110 mmol/l) not only promotes the absorption of sodium but also considerably reduces the duration of the diarrhoea.

Rehydration alone is not sufficient to effectively correct the metabolic acidosis as a result of which the patient is not sufficiently cured. It is therefore that the OR solution must comprise alkalizing substances, for example, bicarbonate or "bicarbonate precursors". The direct alkalizing activity of bicarbonate (and carbonate salts) is based on a neutralization of hydrogen ions. The indirect alkalizing activity of "bicarbonate precursors", for example, citrate, acetate and lactate, is based on the fact that said substances are metabolized in the protonated form. As a result of the unique combination of direct (rapid) and indirect (slowacting) alkalizing substances according to the invention, the metabolic acidosis associated with diarrhoea is effectively controlled without the risk of a hypokalemia (as a result of a too rapid exchange of intracellular $H^+$ ions against extracelular $K^+$ ions).

The commercially available OR products comprise either only bicarbonate (possibility of hypokalemia) or only "bicarbonate precursors" which have first to be metabolized before the acidosis can be controlled effectively (the activity often sets in only after a few hours).

In addition, many commercially available OR products comprise insufficient quantities of alkalizing substances.

The oral effervescent tablet is particularly handy and simple to dose (1 tablet per liter for domestic animals and 1 tablet, for example, per 0.25 or 0.5 liter for companion animals).

The resulting iso-osmotic OR solution comprises:
a. an electrolyte composition with which losses are compensated and with which a rapid rehydration is ensured.
b. lactose and/or maltodextrins, as a result of which the required energy occupies a smaller ($\frac{1}{4}$ to 1/5) part of the osmotic space than with glucose alone.
c. a combination of directly and indirectly acting alkalizing substances, as a result of which the metabolic acidosis is cured safely and effectively.

This combination of ideal electrolyte compositions, high energy-content and direct and indirect acting alkalizing substances in an iso-osmotic OR-solution is unique.

The effervescent composition according to the invention has the following composition:

| Component | Quantity (in mmol/unit of effervescent product necessary for the preparation of 1 liter OR solution) |
|---|---|
| Sodium | 50–150 |
| Potassium | 2–35 |
| Magnesium | 0–5 |
| Calcium | 0–5 |
| Bicarbonate (or carbonate salts) | 20–150 |
| Citric acid (or other solid organic acid) | 5–85 |
| Maltodextrine (or another oligosaccharide) | 0–100 |
| Lactose (or other disaccharide) | 0–200 |
| Glucose (or other monosaccharide) | 0–200 |
| Glycine (or other amino acid or amino acid mixture) | 0–120 |

The composition may be in the form of an effervescent powder or an effervescent tablet. A lubricant may be added for the manufacture of the effervescent tablet. An example of a composition of an effervescent tablet for veterinary application in (young) domestic animals is:

| Component | Quantity (in g) |
|---|---|
| Sodium chloride | 2.34 |
| Potassium chloride | 1.12 |
| Sodium bicarbonate | 6.72 |
| Citric acid 0 aq | 3.84 |
| Glycine | 2.25 |
| Lactose | 32.44 |

When this tablet is dissolved in one liter of water an OR solution is obtained of the following composition:

| Component | Quantity (in mmol/l) |
|---|---|
| $Na^-$ | 120 |
| $K^-$ | 15 |
| $Cl^-$ | 55 |
| $Citrate^{3-}$ | 20[1] |
| $Bicarbonate^-$ | 20 |
| Glycine | 30 |
| Lactose | 90[2] |

[1] equivalent with 20 × 3 = 60 mmol bicarbonate
[2] equivalent with 90 mmol glucose + 90 mmol galactose The pH of the resulting solution is weakly acid (approximately 6.4), which gives a good taste and shelflife of the solution.

An example of a composition of an effervescent tablet for use in companion animals is:

| Component | Quantity (in g) |
|---|---|
| Potassium chloride | 0.56 |
| Sodium bicarbonate | 3.36 |
| Citric acid 0 aq | 1.92 |
| Glycine | 4.13 |
| Maltodextrin | 5.00 |
| Glucose | 5.28 |

When this tablet is dissolved in 0.5 liter of water an OR solution is obtained of the following composition:

| Component | Quantity (in mmol/l) |
|---|---|
| $Na^-$ | 80 |
| $K^-$ | 15 |
| $Cl^-$ | 15 |
| $Citrate^{3-}$ | 20[1] |
| $Bicarbonate^-$ | 20 |
| Glycine | 110 |
| Maltodextrin | 10[2] |
| Glucose | 58.5 |

[1] equivalent with 20 × 3 = 60 mmol bicarbonate
[2] equivalent with 50–60 mmol glucose

I claim:

1. An effervescent product for the preparation of an oral rehydration solution for young domestic animals, wherein the product contains, in g/1 liter of water:

| | |
|---|---|
| sodium chloride | 2.34 |
| potassium chloride | 1.12 |
| sodium bicarbonate | 6.72 |
| anhydrous citric acid | 3.84 |
| glycine | 2.25 |
| lactose | 32.44. | wherein the product is in the form of an effervescent tablet.

2. An effervescent product for the preparation of an oral rehydration solution for companion animals, wherein the product contains in g/0.5 liter of water:

| | |
|---|---|
| potassium chloride | 0.56 |
| sodium bicarbonate | 3.36 |
| anhydrous citric acid [(anhydrous)] | 1.92 |
| glycine | 4.13 |
| maltodextrin | 5.00 |
| glucose | 5.28. | wherein the product is in the form of an effervescent tablet.

3. An effervescent product for the preparation of an oral rehydration solution for domestic animals or companion animals, wherein the product contains, in mmol/unit of effervescent product/1 liter of oral rehydration solution:

| | |
|---|---|
| sodium | [5] 50–150 |
| potassium | 2–35 |
| magnesium | 0–5 |
| calcium | 0–5 |
| bicarbonate [() or carbonate salts ()] | 20–150 |
| citric acid | 5–85 |
| maltodextrin | 0–100 |
| lactose | 0–200 |
| glucose | 0–200 |
| glycine | 0–120. | wherein the carbohydrate to sodium ratio is at least 1:1, and at least one of maltodextrin and lactose is present; such that when the product is to be used in young ruminants, no maltodextrin is present.

4. A product according to claim 3 in the form of an effervescent tablet.

5. A product according to claim 3 in the form of an effervescent powder.

* * * * *